(12) United States Patent
Wang et al.

(10) Patent No.: US 7,179,911 B2
(45) Date of Patent: Feb. 20, 2007

(54) METHOD FOR PREPARING HYDROXAMIC ACIDS

(75) Inventors: Ting-Zhong Wang, Pomona, NY (US);
Lalitha Krishnan, Suffern, NY (US);
Joseph Zeldis, New City, NY (US);
Jeremy I. Levin, New City, NY (US);
Jean Schmid, Chester, NY (US);
Mellard Jennings, Highland Falls, NY (US); Huan-Qiu Li, Brighton, MA (US); Zhixin Wen, Nanuet, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/146,723

(22) Filed: Jun. 7, 2005

(65) Prior Publication Data

US 2005/0272928 A1  Dec. 8, 2005

Related U.S. Application Data

(60) Provisional application No. 60/577,784, filed on Jun. 8, 2004.

(51) Int. Cl.
*C07D 295/26* (2006.01)

(52) U.S. Cl. ............... 544/58.4; 548/262.2; 548/262.4; 548/300.1

(58) Field of Classification Search ............... 544/58.4
See application file for complete search history.

(56) References Cited

U.S. PATENT DOCUMENTS

| 6,153,757 A | 11/2000 | Zook et al. |
| 6,225,311 B1 | 5/2001 | Levin et al. |
| 6,387,901 B1 | 5/2002 | Chupak |

FOREIGN PATENT DOCUMENTS

| WO | WO 97/20824 | 6/1997 |
| WO | WO 98/34918 | 8/1998 |
| WO | WO 03/037852 | 5/2003 |

OTHER PUBLICATIONS

Sorbera et al., "Prinomastat: oncolytic, matrix metalloprotase inhibitor," *Drugs of the Future* (2000) 25(2):150-158.
Shirokova et al., "Novel acyclic nucleotides and nucleoside 5'-triphosphates imitating 2',3'-dideoxy-2',3'-didehydronucleotides: synthesis and biological properties," *J Med Chem* (1994) 37(22):3739-3748.

*Primary Examiner*—Kahsay Habte
(74) *Attorney, Agent, or Firm*—Michael A. Patane; Cozen O'Connor

(57) ABSTRACT

Processes for using a compound of formula III:

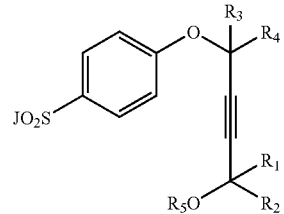

III to make compounds of formulae I and II:

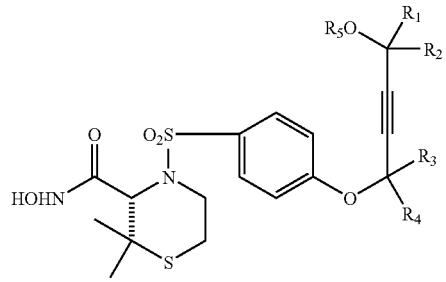

I

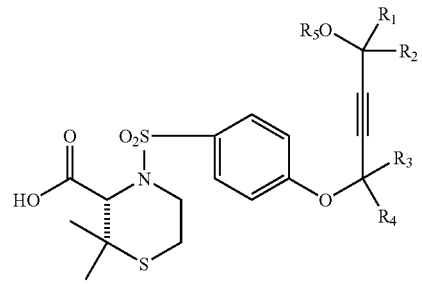

II and processes for making the compound of formula III, where $R_{1-5}$ and J are as defined herein.

26 Claims, No Drawings

METHOD FOR PREPARING HYDROXAMIC ACIDS

CROSS REFERENCE TO RELATED APPLICATIONS

This application claims priority benefit of U.S. Provisional Application Ser. No. 60/577,784 filed Jun. 8, 2004, which is incorporated by reference herein in its entirety.

FIELD OF THE INVENTION

This invention relates to processes for preparing hydroxamic acids and derivatives and intermediates thereof.

BACKGROUND OF THE INVENTION

Hydroxamic acids of formula I

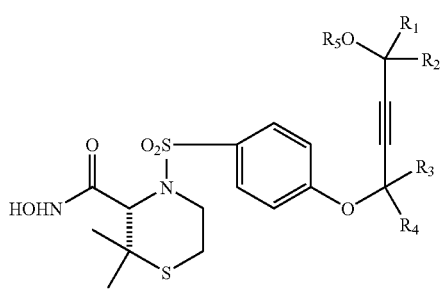

wherein $R_1$ and $R_2$ are independently hydrogen, $C_{1-6}$ alkyl, or —CCH; $R_3$ and $R_4$ are independently hydrogen or $C_{1-6}$ alkyl; and $R_5$ is H, —C(O)—$C_{1-6}$ alkyl, —C(O)—$C_{3-6}$ cycloalkyl, —C(O)-aryl, —C(O)-heteroaryl, —C(O)O—$C_{1-6}$ alkyl, —C(O)O-aryl, or silyl, are inhibitors of TNF-a converting enzyme (TACE) suggesting their potential utilities in the treatment of disease conditions such as rheumatoid arthritis and osteoarthritis (see U.S. Pat. No. 6,225,311 B1, the entire disclosure of which is incorporated by reference herein). Enantiomers can display different TACE-binding activities, and their selectivity and metabolic effects may be different. An efficient, inexpensive and scaleable process for preparing the optically preferred hydroxamic acids is desirable.

SUMMARY OF THE INVENTION

The present invention comprises a process for preparing a compound of formula II:

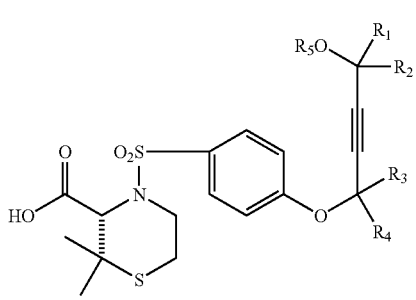

by reacting a compound of formula III:

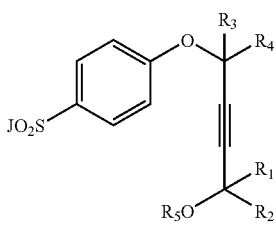

with a silyl ester of (3S)-2,2-dimethyl-tetrahydro-2H-1,4-thiazine-3-carboxylic acid, wherein:

J represents chlorine, bromine, fluorine, 1,2,4-triazolyl, benzotriazolyl or imidazolyl;

$R_1$ and $R_2$ are independently hydrogen, $C_{1-6}$ alkyl, or —CCH;

$R_3$ and $R_4$ are independently hydrogen or $C_{1-6}$ alkyl; and $R_5$ is selected from the group consisting of H, —C(O)—$C_{1-6}$ alkyl, —C(O)—$C_{3-6}$ cycloalkyl, —C(O)-aryl, —C(O)-heteroaryl, —C(O)O—$C_{1-6}$-alkyl, —C(O)O-aryl, and $SiR_6R_7R_8$, where $R_6$, $R_7$ and $R_8$ are each independently selected from the group consisting of $C_{1-6}$ alkyl and phenyl.

The invention further comprises a method for preparing a compound of formula I comprising converting the compound of formula II to a compound of formula I, especially by reaction with hydroxylamine through activation of the carboxylic acid group of the formula II compound, for example by conversion to an acid chloride. The invention also comprises compounds of formula III.

A compound of formula III in which J is a halide may be prepared by reacting a compound of formula IV with a halogenating agent such as thionyl chloride, oxalyl chloride, phosphorus pentachloride, phosphorus oxychloride, thionyl bromide, and the like. The halide may be converted to another J group listed above by reaction with an appropriate compound, such as 1,2,4-triazole, benzotriazole or imidazole. The invention also comprises compounds of formula IV.

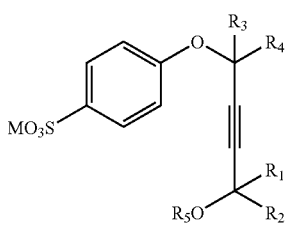

One preferred method for making the compound of formula IV comprises alkylating a compound of formula V, or a salt or solvate thereof with a compound of formula VI to form the compound of formula IV

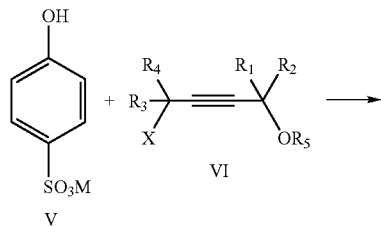

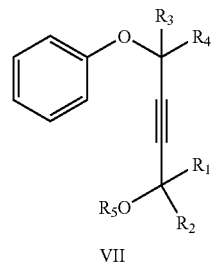

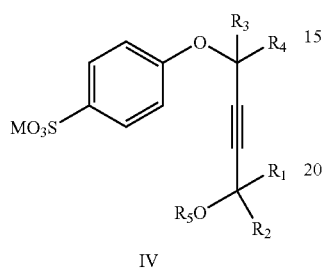

wherein $R_1$ and $R_2$ are each independently hydrogen, $C_{1-6}$ alkyl, or —CCH;

$R_3$ and $R_4$ are each independently hydrogen or $C_{1-6}$ alkyl;

$R_5$ is H, —C(O)—$C_1$ alkyl, —C(O)—$C_{1-6}$ cycloalkyl, —C(O)-aryl, —C(O)-heteroaryl, —C(O)O—$C_{1-6}$-alkyl, —C(O)O-aryl, or $SiR_6R_7R_8$;

$R_6$, $R_7$ and $R_8$ are each independently $C_{1-6}$ alkyl or phenyl;

M is hydrogen or a common metal ion; and

X is a suitable leaving group, such as halogen, mesylate or tosylate.

Preferably, M is hydrogen, lithium, sodium, potassium, cesium, magnesium, copper or zinc.

Alternatively, the invention includes a process whereby compounds of formula IV can be prepared by reacting a compound of formula VIII wherein $M_1$ is lithium, sodium, potassium, zinc or magnesium with a compound of formula IX, followed by acylation with carboxylic acid anhydrides or chlorides to give compounds of formula VII wherein $R_1$ and $R_2$ are each independently hydrogen, $C_{1-6}$alkyl, or —CCH;

$R_3$ and $R_4$ are each independently hydrogen or $C_1$ alkyl; and $R_5$ is —C(O)—$C_{1-6}$ alkyl, —C(O)—$C_{3-6}$ cycloalkyl, —C(O)-aryl, —C(O)-heteroaryl, —C(O)O—$C_{1-6}$-alkyl, or —C(O)O-aryl,

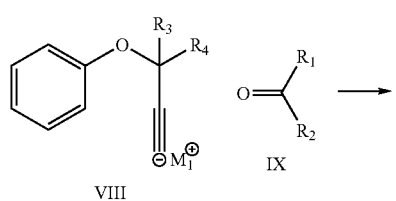

and then reacting the compound of formula VII with chlorosulfonic acid to provide the compound of formula IV wherein M is hydrogen.

DETAILED DESCRIPTION

A preferred embodiment of this invention comprises a process for preparing hydroxamic acids of formula I using a compound of formula II, particularly where all R groups are hydrogen.

In another preferred aspect of the invention, in the compound of formula III all the R groups are hydrogen.

In one preferred embodiment of the process of this invention, in the intermediate compound of formula VI $R_{1-4}$ are all hydrogen and $R_5$ is benzoyl.

Preferably, this compound is prepared by selective protection of 1,4-butyne-2-diol with benzoyl chloride followed by conversion of the hydroxyl group to a suitable leaving group such as mesylate, tosylate, Cl, or Br, for example as shown in Scheme 1, below.

Scheme 1

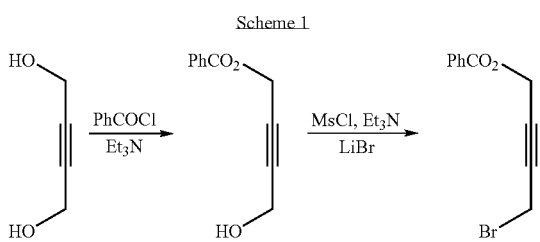

In a preferred embodiment of the present invention, a compound of formula V is alkylated with 4-bromo-but-2-ynyl benzoate to produce sodium 4-(4-hydroxy-but-2-ynyloxy)benzenesulfonate, for example as shown in Scheme 2, below. Other salt forms may also be isolated if bases other than sodium methoxide are used; for example, a potassium salt can be isolated if potassium methoxide is used.

Scheme 2

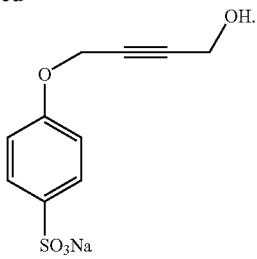

In another preferred embodiment of this invention, a compound of formula IV in which $R_{1-5}$ are all hydrogen and M is sodium, is converted to a compound of formula III where $R_5$ is acetyl and J is chlorine by acetylation of the hydroxyl group with acetic anhydride followed by reaction with oxalyl chloride, as is illustrated below in Scheme 3.

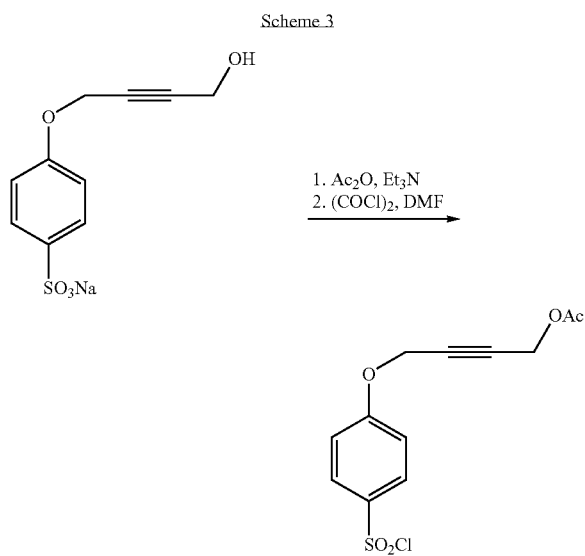

In another preferred embodiment of this invention, illustrated in Scheme 4 below, a compound of formula VIII wherein $M_1$ is lithium and $R_1$ and $R_2$ are hydrogen (prepared in situ by the reaction of phenylpropargyl ether with n-butyllithium in hexanes at low temperature) is reacted with paraformaldehyde to give 1-phenoxy-4-hydroxybut-2-yne which is acetylated in situ with acetic anhydride to give 1-phenoxy-4-acetoxy but-2-yne.

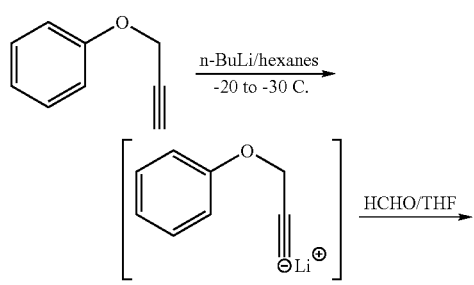

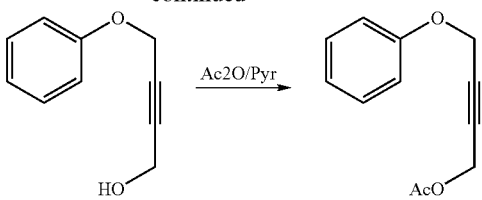

In the preferred embodiment of this invention illustrated in Scheme 5, below, 1-phenoxy-4-acetoxybut-2-yne is chlorosulfonated using chlorosulfonic acid followed by treatment with oxalyl chloride to produce a compound of formula III where $R_5$ is acetyl, and J is chlorine.

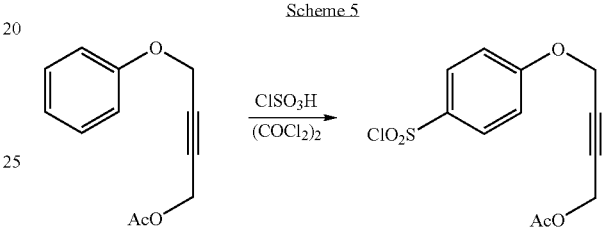

In another preferred aspect of this invention illustrated below in Scheme 6, 4-[4-(chlorosulfonyl)phenoxy]-2-butynyl acetate is coupled with a silyl ester of (3S)-2,2-dimethyl-tetrahydro-2H-1,4-thiazine-3-carboxylic acid followed by transformation of the resulting carboxylic acid of formula II to a hydroxamic acid of formula I where $R_{1-4}$ are hydrogen and $R_5$ is acetyl. (3S)-2,2-dimethyl-tetrahydro-2H-1,4-thiazine-3-carboxylic acid can be synthesized, for example, according to the procedures set forth in U.S. Pat. No. 6,153,757, and the acid group is then protected, preferably as a silyl ester using a silylating agent such as bis(silyl)acetamide (BSA) or N,O-bis(trimethyl-silyl)trifluoroacetamide (BSTFA), and a suitable base such as 4-methylmorpholine. Examples of suitable silyl esters include, but are not limited to, trimethylsilyl, triethylsilyl, triisopropylsilyl, t-butyidimethylsilyl and dimethylthexylsilyl esters. The silyl ester is hydrolyzed to an acid during aqueous work-up after coupling, and the acid must be activated before it can react with hydroxylamine. Activation may be accomplished by converting the acid to an acid chloride using $(COCl)_2$, as shown in Scheme 6 below, or by other means known in the art.

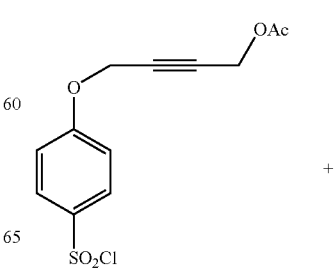

+

-continued

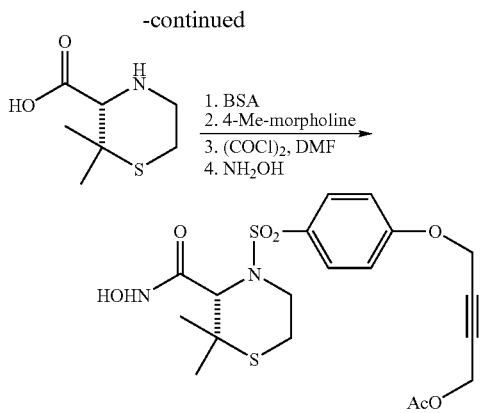

The acetate group in the compound of formula I shown in Scheme 6 may be hydrolyzed chemically, for example using potassium carbonate, or enzymatically using a commercially available lipase preparation or a commercial lipase preparation immobilized on polymeric beads, to make a compound of formula I wherein $R_{1-5}$ are all hydrogen. An example of this process is illustrated in Scheme 7, below.

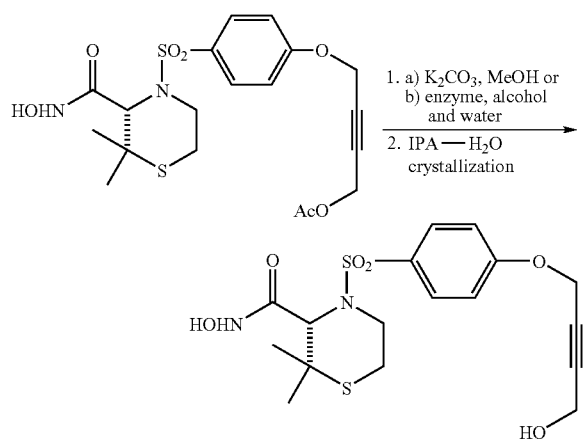

In this specification, when the term "suitable leaving group" is used to describe part of a compound which is to undergo a reaction, this term refers to a group that will readily be replaced when the compound is reacted as indicated. Those skilled in the art will readily understand which groups are suitable leaving groups in the compounds and reactions of this invention. Examples of suitable leaving groups in the practice of this invention include halogen (especially Cl and Br), mesylate, tosylate, and the like.

The term "common metal" as used herein refers to naturally occurring metals having an atomic number less than 80, preferably less than 57. Examples of common metals include Li, Na, K, Mg, Cu, Cs and Zn.

Wherever the term "alkyl" appears herein, it means and includes both straight and branched chain alkyl groups. The term "aryl" as used herein means and includes optionally substituted mono-, di- and tri-cyclic aromatic compounds having 5–14 ring atoms, in which the ring atoms consist entirely of carbon atoms. The term "heteroaryl" as used herein means and includes optionally substituted mono-, di- and tri-cyclic aromatic compounds having 5–14 ring atoms, in which the ring atoms consist of carbon atoms and 1–4 atoms selected from nitrogen, oxygen and sulfur.

Suitable substituents for alkyl, aryl, and heteroaryl groups include, but are not limited to, halogen, $NO_2$, CN, OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, $C_{3-8}$ cycloalkyl, $C_{3-8}$ cycloheteroalkyl, $C_{3-8}$ cycloalkoxy, $C_{3-8}$ cycloheteroalkoxy, aryl, heteroaryl, benzyl, aryloxy, heteroaryloxy, benzyloxy, $NH_2$, NH—$C_{1-6}$ alkyl, N($C_{1-6}$ alkyl)$_2$, NHC(O)—$C_{1-6}$ alkyl, NHC(O)-aryl, $SO_2$—$C_{1-6}$ alkyl, $SO_2$-aryl, $SO_2$-heteroaryl, $SO_2NH$—$C_{1-6}$ alkyl, $SO_2N(C_{1-6}$ alkyl)$_2$, COH, C(O)—$C_{1-6}$ alkyl, C(O)—$C_{3-8}$ cycloalkyl, C(O)—$C_{3-8}$ cycloheteroalkyl, C(O)-aryl, C(O)-heteroaryl, C(O)$NH_2$, C(O)NH—$C_{1-6}$ alkyl, C(O)N($C_{1-6}$ alkyl)$_2$, C(O)OH, C(O)O—$C_{1-6}$ alkyl, C(O)O—$C_{3-8}$ cycloalkyl, C(O)O—$C_{3-8}$ cycloheteroalkyl, C(O)O-aryl, C(O)O-heteroaryl, and the like.

The term "acid-protecting agent" refers to any agent that will protect the carboxylic acid group of (3S)-2,2-dimethyl-tetrahydro-2H-1,4-thiazine-3-carboxylic acid from undesirable side reactions during the coupling reaction of the compound of formula II. Those skilled in the art will be aware of a wide variety of suitable acid protecting agents in addition to those specifically identified herein. The term "silylating agent" refers to an acid-protecting agent that will effect silylation of the carboxylic acid group. The term "acid-protected form" refers to the product formed by reacting (3S)-2,2-dimethyl-tetrahydro-2H-1,4-thiazine-3-carboxylic acid with an acid-protecting group, for example, a silyl ester of (3S)-2,2-dimethyl-tetrahydro-2H-1,4-thiazine-3-carboxylic acid. Those skilled in the art will readily appreciate the identity of various other suitable acid-protected forms of this compound and how to make them.

The term "activation" or "activated" with reference to the carboxylic acid group in the compound of formula II refers to the conversion of the acid group to a form that will more readily react with hydroxylamine. Preferably, the activated acid form is an acid halide, especially an acid chloride. However, those skilled in the art will readily appreciate that other activated forms of the compound may also be used, and may be made by reactions known in the art.

The following examples are presented to illustrate certain embodiments of the present invention, but should not be construed as limiting the scope of this invention. The reagents and solvents for the individual step are given for illustrative purposes only and may be replaced by other suitable reagents and solvents known to those skilled in the art.

EXAMPLE 1

PREPARATION OF 4-PHENOXY-2-BUTYNYL ACETATE

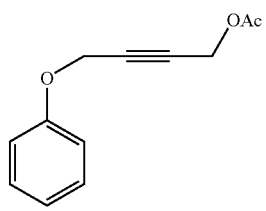

A 0.5-L reactor (#1) was equipped with a thermometer, an addition funnel, an overhead stirrer, and a nitrogen inlet. 150 mL of THF was charged followed by 27.5 g (0.21 mole) of phenyl propargyl ether. The solution was cooled to −20° C. 100 mL (0.25 mole) of n-butyllithium in hexanes was charged into an addition funnel. This solution was added to the reactor at a temperature between −25 and −35° C. The temperature was controlled by the rate of addition and the mixture was stirred for 1 h at −25 to −35° C. A second 1-L reactor (#2) was equipped with a thermometer, an overhead stirrer and a cannulation device. 120 mL of THF was charged followed by 9.4 g (0.42 mol) of paraformaldehyde as a solid in one portion. The resulting suspension was stirred for 5 min. and cooled to 5–10° C. The contents of reactor #1 were cannulated into reactor #2 maintaining temperature in reactor #2 between 5 and 15° C. The temperature in reactor #1 was maintained below −15° C. The cooling bath from reactor #2 was removed and the reaction mixture was allowed to warm up slowly to 20–25° C. Stirring was continued for 16 h at ambient temperature. 200 mL of water was added to the reaction mixture and the mixture was stirred for 15–30 min at ambient temperature. The reaction mixture was extracted twice with 200 mL and then 100 mL of ethyl acetate. The combined organic solution was washed with 200 mL of water. The organic solution was dried with 50 g of anhydrous sodium sulfate. The drying agent was filtered off and rinsed with 50 mL of ethyl acetate. The filtrate was transferred into a 1-L reactor fitted with an overhead stirrer. Pyridine (67 mL, 0.83 mol) was charged followed by acetic anhydride (39 mL, 0.42 mol). The solution was stirred overnight at ambient temperature. The solution was washed sequentially with water (200 mL), sodium bicarbonate solution (2×150 mL) until pH=7–8, hydrochloric acid solution (2×150 mL) until pH=1–3, and brine (1×150 mL). The solution was dried with anhydrous sodium sulfate (50 g). The drying agent was filtered off, and the filtrate was concentrated in vacuo at a temperature that did not exceed 60° C. to yield 37 g (87% yield, HPLC strength 65%) of product as a dark-red slightly viscous fluid.
$^1$H NMR (300 MHz, CDCl$_3$) δ 7.0–7.3 (m, 5H, C$_6$H$_5$), 4.7 (s, 4H), 2.1 ( s, 3H) 2H).

EXAMPLE 2

CHLOROSULFONATION OF 4-PHENOXY-2-BUTYNYL ACETATE

4-[4-(Chlorosulfonyl)PHENOXY]-2-Butynyl Acetate

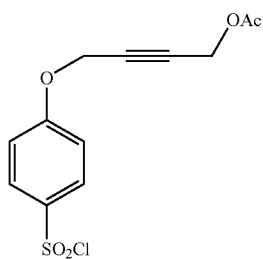

A 22-L reactor was equipped with a thermometer, a water condenser, a cooling bath/heating mantle, and an addition funnel, and dichloromethane (11 L) was charged. A solution of 4-phenoxy-2-butynyl acetate in dichloromethane (2.04 kg, 10 mol) was charged to the reactor, followed by 2 L of dichloromethane and the solution was cooled −5 to −10° C. Chlorosulfonic acid (0.73 L, 1.28 kg, 11 mol) was added slowly via an addition funnel maintaining temperature between −5 and 0° C. After the addition was complete, the cooling bath was removed and the reaction mixture was stirred for 1–2 h at 18–22° C. The progress of the reaction was monitored by TLC or HPLC (disappearance of starting material). DMF (155 mL, 146 g) was added portion wise. The reaction mixture was heated to reflux (38–40° C.). Oxalyl chloride (1.13 L, 1.65 kg, 13 mol) was added through an addition funnel into the boiling solution over a period of 2–3 h maintaining gentle reflux. After all the oxalyl chloride was added, reflux was continued for 1 h. The completion of reaction was checked by HPLC (less than 3% of intermediate sulfonic acid remaining). After completion, the heating was stopped and the reaction mixture was cooled to 18–22° C. and stirred for 16 h. The reaction mixture was quenched into a 50-L reactor with 5 L of cold (5 to 10° C.) water and stirred for 10–20 min while maintaining the temperature below 20° C. The organic layer was separated and the aqueous layer was extracted with (2 L) of fresh dichloromethane. The combined organic layers were washed with 4 L of sodium bicarbonate solution until pH=7–8. The dichloromethane layer was separated and concentrated in vacuo at 35–40° C. to a volume of 5 to 7 L. This solution was mixed with 3 kg of silica gel and concentrated in vacuo until a free-flowing powder was obtained. The silica gel powder was transferred to a filter funnel with a Celite bed and eluted with 22 L of isopropyl ether. The ether solution was concentrated in vacuo to yield about 3 L of a slightly viscous liquid. This residue was transferred to a 5-L reaction flask with overhead stirrer, seeded and stirred for 16–18 h at 18–22° C. Crystallization began after several hours. Stirring continued at low temperature (0 to −10° C.). The solid was filtered on Buchner funnel lined with polypropylene and washed with 2 L of cold (5° C.) IPE, then dried under vacuum (30 mm) at 18–20° C. to yield 1.1 kg (55%, HPLC strength 94.8%) of product.
$^1$H NMR (300 MHz, CDCl$_3$) δ 8.01 (m, 2H), 7.12 (m, 2H), 4.86 (t, J=1.8 Hz, 2H), 4.72 (t, J=1.8 Hz, 2H), 2.10 (s, 3H); $^{13}$C NMR (75 MHz, CDCl$_3$) ppm 170.5, 163.0, 137.2, 129.9, 116.0, 83.3, 80.2, 56.8, 52.3, 21.0.

EXAMPLE 3

BENZOYLATION OF 2-BUTYNE-1,4-DIOL

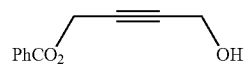

2-Butyne-1,4-diol (880 g, 10.2 mol) was dissolved in tetrahydrofuran (4 L) in a 4-neck 12-L flask equipped with an overhead stirrer, a thermocouple and an addition funnel. Triethylamine (567 g, 5.6 mol) was added to the flask. The resulting solution (10–15° C.) was cooled to 0° C. Benzoyl chloride (721 g, 5.1 mol) was added via the addition funnel while temperature of the mixture was maintained at 0–15° C. (42 min of addition time). The mixture was then allowed to warm to room temperature, and was monitored for complete consumption of benzoyl chloride by HPLC (<2%). The solution was concentrated in vacuo (45–55° C., 115–145 mmHg), yielding about 3.5 L of residue. Toluene (3.8 L) was added to the flask, and distillation was continued until the final volume reached about 6 L. After the mixture was cooled to room temperature, water (3.3 L) was added. The mixture was stirred for 2 min, and the phases were separated. The organic phase was washed with water (2×2.7 L) and was checked for diol content by GC/MS (<2%). The toluene was distilled off to give 1.25 kg of yellow oil, which contained about 30% of toluene. The crude product had HPLC weight strength of 51% for 4-hydroxy-but-2-ynyl benzoate (yield of ~60%). Water content by KF test was 0.03%. A small analytical sample was purified by chromatography (eluted with 40% EtOAc/Hexanes): $^1$H NMR (300 MHz, CDCl$_3$) δ 8.07 (m, 2H), 7.58 (m, 1H), 7.45 (m, 2H), 4.96 (t, J=1.8 Hz, 2H), 4.34 (dt, J=6.3, 1.8 Hz, 2H), 1.93 (t, J=6.3 Hz, 1H); $^{13}$C NMR (75 MHz, CDCl$_3$) ppm 166.5, 133.8, 130.2, 129.8, 128.3, 85.7, 80.1, 53.2, 51.3.

EXAMPLE 4

CONVERSION OF 4-HYDROXY-BUT-2-YNYL BENZOATE TO 4-Bromo-But-2-Ynyl Benzoate

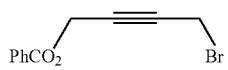

The crude product from Example 3 (1.23 kg, 3.21 mol) was dissolved in toluene (5.2 L) in a 4-neck 12-L flask equipped with an overhead stirrer, a thermocouple and an addition funnel. The solution was cooled to 0° C. before triethylamine (399 g, 3.94 mol) was added. Methanesulfonyl chloride (435 g, 3.8 mol) was added via the addition funnel while the temperature was maintained at 0–15° C. (addition time of 30 min). The mixture was stirred at 10–20° C. for 30 min. The reaction progress was monitored by HPLC (<2% of S.M.). Lithium bromide (546 g, 6.28 mol) was added in one portion. Tetrahydrofuran (750 mL) was added over 50 min while the temperature was maintained at 10–20° C. The mixture was stirred at 20° C. for 2 h and monitored by HPLC for complete reaction (<2% mesylate). Water (3.4 L) was introduced over 3 min, and the phases were separated. The organic phase was washed with 5% aqueous sodium bicarbonate solution (2.6 L) and water (2×2.6 L). The toluene was distilled off in vacuo (60° C., 110 mmHg) to give 1.4 kg of crude product containing 26% of toluene. The crude product contained about 60% of 4-bromo-but-2-ynyl benzoate by HPLC weight strength. A small analytical sample was purified by chromatography (elution with 10% EtOAc/Hexanes): $^1$H NMR (300 MHz, CDCl$_3$) δ 8.07 (m, 2H), 7.58 (m, 1H), 7.46 (m, 2H), 4.98 (t, J=2.0 Hz, 2H), 3.96 (t, J=2.0 Hz, 2H); $^{13}$C NMR (75 Hz, CDCl$_3$) ppm 165.9, 133.4, 129.9, 129.4, 128.5, 81.9, 80.8, 52.7, 13.9.

EXAMPLE 5

PREPARATION OF 4-(4-HYDROXY-BUT-2-YNYLOXY)-BENZENESULFONIC ACID, SODIUM SALT

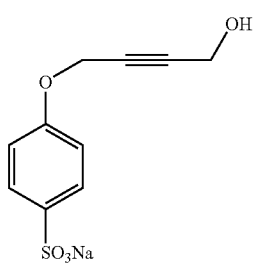

To solid 4-hydroxybenzenesulfonic acid sodium salt dihydrate (352 g, 1.51 mol) in 4-neck 5-L flask equipped with an overhead stirrer, a condenser and a thermocouple, was added 1.66 L of 1 N sodium methoxide solution in methanol and tetrabutylammonium bromide (14.3 g, 0.044 mol). The suspension was heated at 65° C. for 30 min. 4-Bromo-but-2-ynyl benzoate from Example 4 (750 g, 60% of strength, 1.78 mol) was added over 40 min. The mixture was heated for 3 h at 65° C. before additional bromide (270 g, 0.64 mol) and sodium methoxide solution (74 g of 25 wt % solution, 0.36 mol) were added over 20 min. Heating at 65° C. was continued for 3 h, and HPLC analysis indicated that about 8% of the starting sodium salt remained. The solution was concentrated in vacuo to a residual volume of 2.6 L. The mixture was cooled to ambient temperature overnight and then to 2° C. for 35 min. The solid product was collected by filtration and washed with THF (3×450 mL). The solid was air-dried to a constant weight (376 g). The crude product was dissolved in 1.12 L of water by heating to 65° C. Tetrahydrofuran (410 mL) was added over 17 min. The solution was slowly cooled to 25° C. over 3 h and then cooled further to 5° C. for 45 min. Crystals were collected by filtration and washed with 2×0.3 L of an ice-cold mixture of water/THF (7:3), then THF (0.3 L). The solid was air-dried to a constant weight (310 g) before it was further dried in vacuo (1.5 mmHg) at 80° C. The final product weighed 272 g (68% yield based on sulfonic acid sodium salt): $^1$H NMR (300 MHz, DMSO-d$_6$) δ 7.53 (m, 2H), 6.90 (m, 2H), 5.25 (t, J=6.3 Hz, 1H), 4.83 (t, J=1.6 Hz, 2H), 4.10 (dt, J=6.3, 1.6 Hz, 2H); $^{13}$C NMR (75 MHz, D$_2$O) ppm 159.5, 136.1, 127.8, 115.5, 86.4, 80.2, 56.6, 49.9.

EXAMPLE 6

PREPARATION OF 4-(4-ACETOXY-BUT-2-YNYLOXY)-BENZENESULFONIC ACID, SODIUM SALT

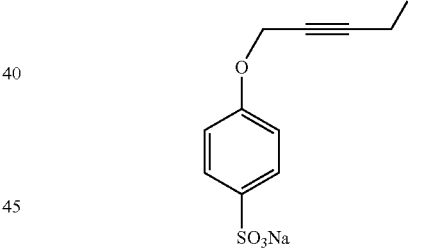

To a suspension of 4-(4-hydroxy-but-2-ynyloxy)-benzenesulfonic acid, sodium salt from Example 3 (350 g, 1.32 mol) in tetrahydrofuran (2.24 L) in a 5 L 4-neck flask, was added triethylamine (215 mL, 156 g, 1.54 mol) and 4-dimethylaminopyridine (9.1 g, 0.074 mol). Acetic anhydride (251 mL, 272 g, 2.66 mol) was added over 10 min. The mixture was slowly heated to 65° C. over 35 min, and maintained at 65° C. for 2 h. The reaction was monitored for completion by HPLC (S.M<3%). Water (125 g) was carefully added over 10 min while the temperature was maintained at 60–70° C. The mixture became a clear solution, and was slowly cooled to 23° C. over 3 h. Upon further cooling at 2° C. for 1 h, the crystals were collected by filtration and washed with tetrahydrofuran (2×0.55 L). The solid was air-dried to a constant weight (392 g) and then dried in vacuo (1.5 mmHg) at 85° C. to yield 350 g of product (86% yield): $^1$H NMR (300 MHz, DMSO-d$_6$) δ 7.53 (m, 2H), 6.90 (m, 2H), 4.86 (t, J=1.6 Hz, 2H), 4.74 (t, J=1.6 Hz, 2H), 2.04 (s, 3H); $^{13}$C NMR (75 MHz, DMSO-d$_6$) ppm 170.0, 157.6, 141.6, 127.4, 114.1, 82.1, 82.0, 55.9, 52.0, 20.8.

EXAMPLE 7

PREPARATION OF 4-[4-(CHLOROSULFONYL)PHENOXY]-2-BUTYNYL ACETATE

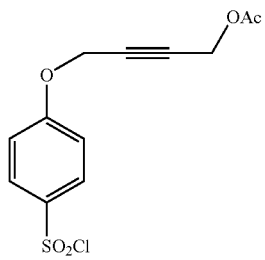

To a suspension of 4-(4-acetoxy-but-2-ynyloxy)-benzenesulfonic acid, sodium salt from Example 6 (360 g, 1.18 mol) in 2.1 L of dichloromethane in a 5-L 4-neck flask, was added N,N-dimethylformamide (14 g, 0.19 mol) and water (4.5 g, 0.25 mol). The mixture was cooled to 12° C. Oxalyl chloride (165 mL, 240 g, 1.89 mol) was added over 70 min while the temperature was maintained at 10–20° C. The mixture was slowly warmed to 23° C. over 1 h and stirred at this temperature for 1 h. The reaction was monitored for completion by HPLC (S.M. <3%). The mixture was quenched into 2 L of water in a 12-L flask at 30° C. After 5 min of stirring, the phases were separated and the organic phase was washed with water (1 L). The mixture was held at 0–5° C. overnight, resulting in clear phase separation. Dichloromethane was distilled off to a residual volume of about 700 mL. t-Butyl methyl ether (1.5 L) was added. Distillation was continued to a residual volume of 850 mL. The solution was cooled to 18° C. and seeded with crystals. After 35 min of stirring, product crystals formed. Heptane (650 mL) was added over 40 min while the temperature was maintained at 15–20° C. The mixture was heated to 35° C. to dissolve the product before it was cooled back to 20° C. More heptane (350 mL) was added over 10 min. The mixture was stirred at 15–20° C. for 40 min. The crystals were filtered in a funnel and washed with heptane (400 mL). The product was dried in vacuo at 23° C. to a constant weight (316 g, 89% yield). $^1$H NMR (300 MHz, CDCl$_3$) δ 8.01 (m, 2H), 7.12 (m, 2H), 4.86 (t, J=1.8 Hz, 2H), 4.72 (t, J=1.8 Hz, 2H), 2.10 (s, 3H); $^{13}$C NMR (75 MHz, CDCl$_3$) ppm 170.5, 163.0, 137.2, 129.9, 116.0, 83.3, 80.2, 56.8, 52.3, 21.0.

EXAMPLE 8

PREPARATION OF (3S)-N-HYDROXY-4-({4-[(4-ACETOXY-2-BUTYNYL)OXY]PHENYL}SULFONYL)-2,2-DIMETHYL-3-THIOMORPHOLINE CARBOXAMIDE

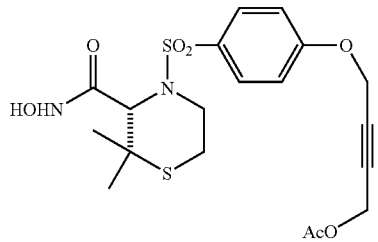

A suspension of (3S)-2,2-dimethyl-tetrahydro-2H-1,4-thiazine-3-carboxylic acid (173.7 g, 1.0 mol) in dichloromethane (1.4 L) in a 12 L 3-neck flask equipped with an overhead stirrer, heating mantle, thermocouple, and condenser was heated to reflux (40–41° C.) over 15 min. N,O-bis(trimethyl-silyl)trifluoroacetamide (BSTFA) (515 g, 2.0 mol) was added over 30 min. The reaction mixture was stirred at reflux until clear (1–2 h). The clear solution was cooled to 5–10° C. with an ice-bath, then N-methylmorpholine (143 mL, 132 g, 1.3 mol) was added over 5–10 min. A solution of sulfonyl chloride from Example 5 (300 g, 1.0 mol) in dichloromethane (0.7 L) was added to the reaction mixture while maintaining the temperature between 5–10° C. After 15 min of stirring, the ice-bath was removed and the solution was allowed to warm to room temperature. After overnight stirring, the reaction mixture was cooled to 5–10° C. with an ice-bath then DMF (30.9 mL, 29.2 g, 0.4 mol) was added over 5 min through an addition funnel followed by oxalyl chloride (319 g, 2.5 mol). Temperature was maintained between 5 and 15° C. Precipitates formed during addition. The reaction mixture was warmed to room temperature and stirred for 18 h. The mixture turned cherry red as the reaction proceeded. The acid chloride mixture was then cannulated into another 12 L 3-neck flask with THF (1.5 L), water (1.0 L) and 50% aq. solution of hydroxylamine (430 mL, 7.0 mol) maintaining temperature between 0–20° C. The cooling bath was then removed to allow the solution to warm to room temperature over 1.5 h. Water (2.0 L) was added to allow phase separation. The bottom organic layer was concentrated in vacuo to a volume of 1.8 L (heating temperature 37–52° C.) then ethyl acetate (1.2 L) was added and concentrated again to a volume of about 1.5 L. After allowing the mixture to stand at room temperature overnight, the crystals obtained were filtered into a Buchner funnel and washed with ice-cold ethyl acetate (5° C., 2×0.75 L). The product was air-dried, dired in vacuo under rubber dam at room temperature overnight, and dried in a vacuum oven at 40–41° C. to give 273 g (60% yield) of a light beige solid. $^1$H NMR (300 MHz, CDCl$_3$) 9.67 (s, NH), 7.73 (d, 2H, J=8.9 Hz), 7.01 (d, 2H, J=8.9 Hz), 4.78 (s, 2H), 4.71 (s, 2H), 4.53 (s, 1H), 3.94.1 (m, 1H), 3.0–3.4 (m, 2H), 2.4–2.6 (m, 1H), 2.11 (s, 3H), 1.60 (s, 3H), 1.29 (s, 3H).

EXAMPLE 9

PREPARATION OF (3S)-N-HYDROXY-4-({4-[(4-HYDROXY-2-BUTYNYL)OXY]PHENYL}SULFONYL)-2,2-DIMETHYL-3-THIOMORPHOLINE CARBOXAMIDE

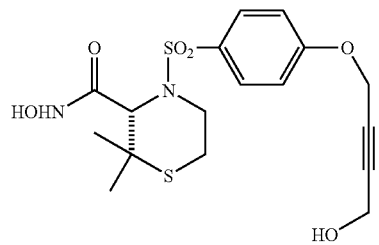

(3S)-N-hydroxy-4-({4-[(4-acetoxy-2-butynyl)oxy]phenyl}sulfonyl)-2,2-dimethyl-3-thiomorpholine carboxamide from Example 6 (120 g, 0.26 mol) was suspended in 2.2 L of methanol under an inert atmosphere. The reaction mixture was warmed to 40–45° C. to effect dissolution. After dissolution of the solid, the mixture was cooled to 22–25-° C. 36.3 g (0.26 mol) of potassium carbonate was dissolved in 364 mL of water, and 360 mL of the solution was added to the reaction mixture between 22–32° C. The solution was warmed to 32° C. to effect complete dissolution (pH=11.0–11.3). The reaction was monitored by HPLC and was complete in 1 h. About 400 mL of 1 N HCl was added to the reaction mixture with stirring to adjust the pH between 5.6 and 6.0. The reaction mixture was clarified by filtering through a Buchner funnel lined with polypropylene and the filtrate was concentrated to approximately one third the original volume at 35–40° C. in vacuo. The mixture was stirred for 1 h at 5–10° C., filtered and washed with 3×120 mL of water. The wet solid (105 g) was added to a mixture of 368 mL of isopropanol and 158 mL of water. The mixture was warmed to 51–55° C. until all the solids had dissolved and a clear solution was obtained. 1.2 L of water was added over 1 h maintaining the temperature between 51 and 55° C. The temperature of the solution was maintained at 51–55 with stirring for 3 h. The solution was then allowed to cool gradually to 22–24° C. and stirred overnight. The solution was then cooled to 5–10° C. with stirring for 1 h. The solids were filtered and dried in an oven at 50° C. for 72 h in vacuo to yield 93 g of product (85% yield). LC area % 99.3, KF 1.0%, IPA 0.5%, DSC: $T_{apex}$ 145° C. $^1$H NMR (CD$_3$OD): δ 1.45 (d, 6H), 2.52 (m, 1H), 3.07 (m, 2H), 3.9 (m, 2H), 4.14 (s,2H), 4.37 (s, 2H), 7.12 (d, 2H), 7.71 (d, 2H). HPLC (area % 99, Strength 98%).

Many variations of the present invention not illustrated herein will occur to those skilled in the art. The present invention is not limited to the embodiments illustrated and described herein, but encompasses all the subject matter within the scope of the appended claims and equivalents thereof.

What is claimed is:

1. A process for making a compound of formula II:

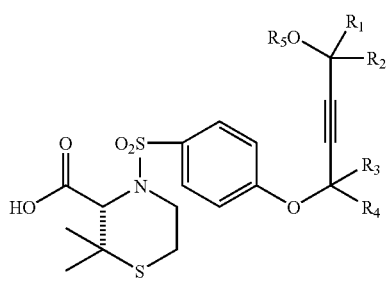

comprising reacting a silyl ester of (3S)-2,2-dimethyl-tetrahydro-2H-1,4-thiazine-3-carboxylic acid with a compound of formula III:

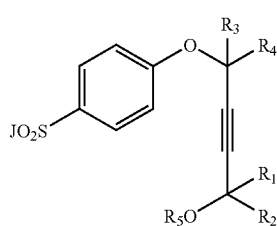

wherein:
J is selected from the group consisting of chlorine, bromine, fluorine, 1,2,4-triazolyl, benzotriazolyl and imidazolyl;
$R_1$ and $R_2$ are each independently selected from the group consisting of H, $C_{1-6}$ alkyl, and —CCH;
$R_3$ and $R_4$ are each independently selected from the group consisting of H and $C_{1-6}$ alkyl;
$R_5$ is selected from the group consisting of H, —C(O)—$C_{1-6}$ alkyl, —C(O)—$C_{3-6}$ cycloalkyl, —C(O)-aryl, —C(O)-heteroaryl, —C(O)O—$C_{1-6}$ alkyl, —C(O)O-aryl, and SiR$_6$R$_7$R$_8$; and
$R_6$, $R_7$ and $R_8$ are each independently selected from the group consisting of $C_{1-6}$ alkyl and phenyl; and
hydrolyzing the silyl ester to provide the compound of Formula II.

2. The process of claim 1 further comprising activating the carboxylic acid group of the compound of formula II and reacting the activated compound of formula II with hydroxylamine; to provide a compound of formula I:

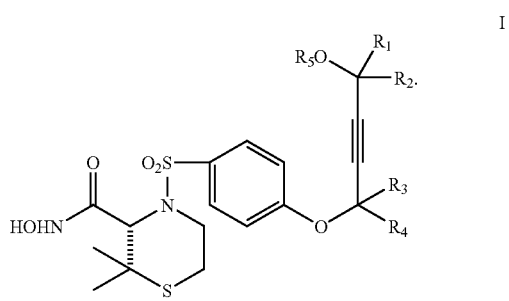

3. The process of claim 2, wherein $R_5$ is selected from the group consisting of —C(O)—$C_{1-6}$ alkyl, —C(O)—$C_{3-6}$ cycloalkyl, —C(O)-aryl, —C(O)-heteroaryl, —C(O)O—$C_{1-6}$ alkyl, —C(O)O-aryl, and SiR$_6$R$_7$R$_8$.

4. The process of claim 3, wherein the compound of formula I is treated with a base to produce a compound of formula I wherein $R_5$ is H.

5. The process of claim 1 wherein the compound of formula III is prepared by a process comprising the step of reacting a halogenating reagent with a compound of formula IV:

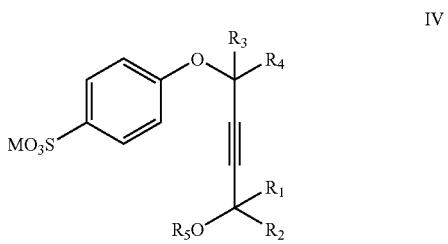

wherein M is selected from the group consisting of H and an ion of a naturally occurring metal having an atomic number less than 80.

6. The process of claim 5 wherein M is selected from the group consisting of H, Li, Na, K, Mg, Cu, Cs and Zn.

7. The process of claim 5 wherein said halogenating agent is selected from the group consisting of thionyl chloride, oxalyl chloride, phosphorus pentachloride, phosphorus oxychloride, and thionyl bromide.

8. The process of claim 5 wherein the compound of formula IV is prepared by a process comprising the step of reacting a compound of formula V:

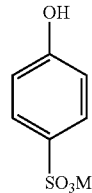

with a compound of formula VI:

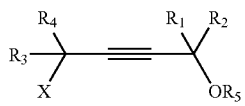

wherein X is a suitable leaving group and M is selected from the group consisting of H and an ion of a naturally occurring metal having an atomic number less than 80.

9. The process of claim 8 wherein M is selected from the group consisting of H, Li, Na, K, Mg, Cu, Cs and Zn, and X is selected from the group consisting of halogen, tosylate and mesylate.

10. The process of claim 9 wherein $R_{1-4}$ are hydrogen, and in the compound of formula VI, $R_5$ is benzoyl.

11. The process of claim 10 wherein the process of producing the compound of formula IV takes place in the presence of a base, producing a compound of formula IV wherein $R_5$ is hydrogen.

12. The process of claim 10 wherein the process of producing the compound of formula IV takes place in the presence of $MOCH_3$, methanol, and tetrabutylammonium bromide, producing a compound of formula IV wherein $R_5$ is hydrogen.

13. The process of claim 10 wherein the compound of formula VI is prepared by a process comprising the steps of selectively protecting one hydroxyl group of but-2-yne-1,4-diol and converting the unprotected hydroxyl group to X.

14. The process of claim 13 wherein the selective protection of one hydroxyl group of but-2-yne-1,4-diol and the conversion of the unprotected hydroxyl group to X are performed sequentially in one pot.

15. The process of claim 5 wherein M is H and the compound of formula IV is prepared by a process comprising the step of reacting $HSO_3Cl$ with a compound of formula VII:

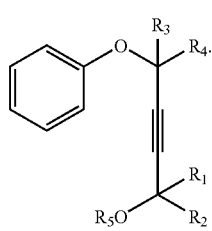

16. The process of claim 15 wherein the compound of formula VII is prepared by a process comprising the step of reacting a compound of formula VIII:

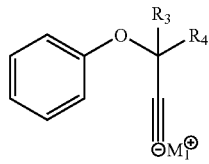

with a compound of formula IX:

wherein $R_5$ is H, and $M_1$ is selected from the group consisting of lithium, sodium, potassium, zinc and magnesium.

17. The process of claim 16 further comprising the step of treating the compound of formula VII wherein $R_5$ is H with a carboxylic acid anhydride or chloride to form a compound of formula VII wherein $R_5$ is selected from the group consisting of —C(O)—$C_{1-6}$ alkyl, —C(O)—$C_{3-6}$ cycloalkyl, —C(O)-aryl, —C(O)-heteroaryl, —C(O)O—$C_{1-6}$ alkyl, and —C(O)—$C_{1-6}$ aryl.

18. A process for making a compound of formula I:

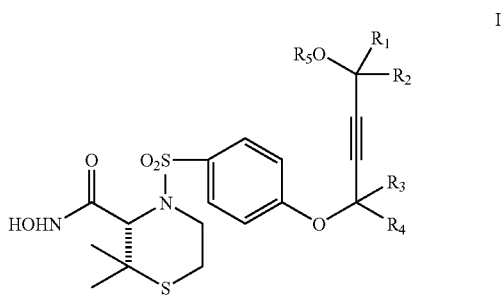

wherein:
$R_1$ and $R_2$ are each independently selected from the group consisting of H, $C_{1-6}$ alkyl, and —CCH,
$R_3$ and $R_4$ are each independently selected from the group consisting of H and $C_{1-6}$ alkyl, and
$R_5$ is selected from the group consisting of H, —C(O)—$C_{1-6}$ alkyl, —C(O)—$C_{3-6}$ cycloalkyl, —C(O)-aryl, —C(O)-heteroaryl, —C(O)O—$C_{1-6}$ alkyl, —C(O)O-aryl, and $SiR_6R_7R_8$, and $R_6$, $R_7$ and $R_8$ are each independently selected from the group consisting of $C_{1-6}$ alkyl and phenyl, said process comprising the step of reacting a halogenating agent with a compound of formula IV:

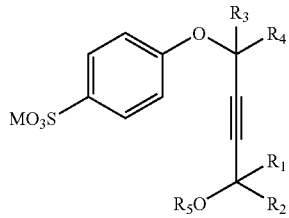

IV to form a compound of formula III:

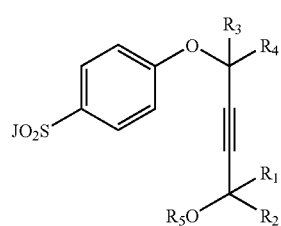

III wherein J is selected from the group consisting of chlorine, bromine and fluorine, and M is selected from the group consisting of H, Li, Na, K, Mg, Cu, Cs and Zn, and, optionally, further reacting the halogenated compound of formula III with 1,2,4-triazole, benzotriazole or imidazole to form another compound of formula III, wherein J is selected from the group consisting of 1,2,4-triazolyl, benzotriazolyl and imidazolyl.

19. The process of claim 18 further comprising the steps of: reacting a silyl ester of (3S)-2,2-dimethyl-tetrahydro-2H-1,4-thiazine-3-carboxylic acid with the compound of formula III to form a compound of formula II:

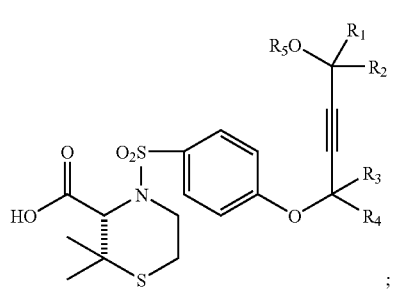

II reacting the compound of formula II with a carboxylic acid group activating agent; and
reacting the activated compound of formula II with hydroxylamine to form the compound of formula I.

20. The process of claim 19, wherein said steps of reacting the compound of formula III with a silyl ester of (3S)-2,2-dimethyl-tetrahydro-2H-1,4-thiazine-3-carboxylic acid to form the compound of formula II, reacting the compound of formula II with a carboxylic acid group activating agent, and reacting the activated compound of formula II with hydroxylamine to form the compound of formula I are all performed sequentially in one pot.

21. The process of claim 19, wherein $R_5$ is selected from the group consisting of —C(O)—$C_{1-6}$ alkyl, —C(O)—$C_{3-6}$ cycloalkyl, —C(O)-aryl, —C(O)-heteroaryl, —C(O)O—$C_{1-6}$ alkyl, —C(O)O-aryl, and $SiR_6R_7R_8$.

22. The process of claim 21, wherein the compound of formula I is treated with a base to produce a compound of formula I wherein $R_5$ is H.

23. A process for making a compound of formula I:

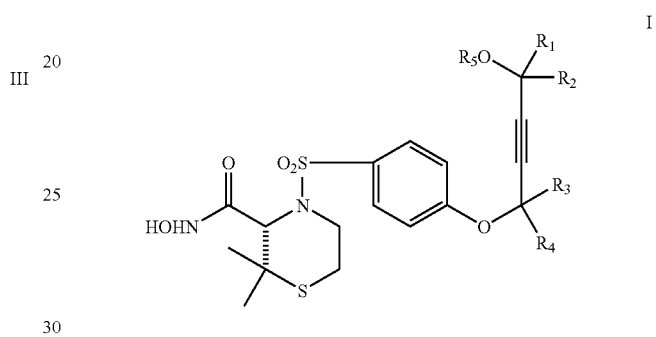

I wherein
$R_1$ and $R_2$ are each independently selected from the group consisting of H, $C_1$–$C_6$alkyl, and —CCH,
$R_3$ and $R_4$ are each independently selected from the group consisting of H and $C_1$–$C_6$alkyl, and
$R_5$ is selected from the group consisting of H, —C(O)—$C_{1-6}$ alkyl, —C(O)—$C_{3-6}$ cycloalkyl, —C(O)-aryl, —C(O)-heteroaryl, —C(O)O—$C_{1-6}$alkyl, —C(O)O-aryl, and $SiR_6R_7R_8$, and
$R_6$, $R_7$ and $R_8$ are each independently selected from the group consisting of $C_1$–$C_6$alkyl and phenyl, said process comprising the steps of:
a) reacting (3S)-2,2-dimethyl-tetrahydro-2H-1,4-thiazine-3-carboxylic acid with a silylating agent to produce a silyl ester of (3S)-2,2-dimethyl-tetrahydro-2H-1,4-thiazine-3-carboxylic acid;
b) reacting the the silyl ester of (3S)-2,2-dimethyl-tetrahydro-2H-1,4-thiazine-3-carboxylic acid with a compound of formula III:

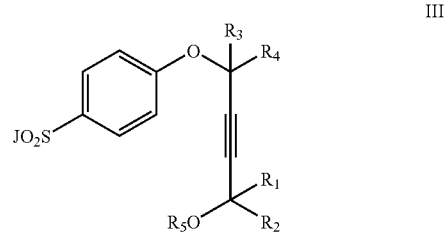

III to form a compound of formula II:

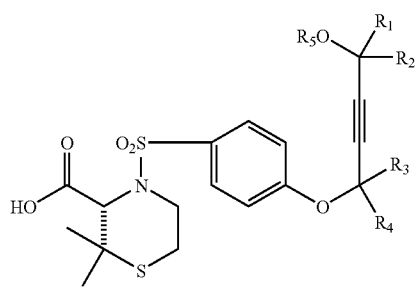

wherein J is selected from the group consisting of chlorine, bromine, fluorine, 1,2,4-triazolyl, benzotriazolyl and imidazolyl;

c) reacting the compound of formula II with a carboxylic acid group activating agent; and d) reacting the activated compound of formula II with hydroxylamine to form the compound of formula I.

24. The process of claim 23, wherein steps a) through d) are performed sequentially in one pot.

25. The process of claim 23, wherein $R_5$ is selected from the group consisting of —C(O)—$C_{1-6}$ alkyl, —C(O)—$C_{3-6}$ cycloalkyl, —C(O)-aryl, —C(O)-heteroaryl, —C(O)O—$C_{1-6}$ alkyl, —C(O)O-aryl, and $SiR_8R_7R_8$.

26. The process of claim 25, wherein the compound of formula I is treated with a base to produce a compound of formula I wherein $R_5$ is H.

* * * * *